United States Patent
Choi et al.

(10) Patent No.: US 7,393,977 B2
(45) Date of Patent: Jul. 1, 2008

(54) DICARBOXYLIC ACID SALT OF SIBUTRAMINE

(75) Inventors: Kwang Do Choi, Gyeonggi-do (KR); Yong Sik Youn, Gyeonggi-do (KR); Hea Ran Suh, Gyeonggi-do (KR); Dong Kwon Lim, Gyeonggi-do (KR); Eun Young Yang, Gyeonggi-do (KR); Jae Kyoung Ko, Incheon (KR); Chang Ju Kim, Gyeonggi-do (KR)

(73) Assignee: CJ Cheiljedang Corporation (KR)

( * ) Notice: Subject to any disclaimer, the term of this patent is extended or adjusted under 35 U.S.C. 154(b) by 0 days.

(21) Appl. No.: 10/580,132

(22) PCT Filed: Jan. 6, 2006

(86) PCT No.: PCT/KR2006/000071

§ 371 (c)(1),
(2), (4) Date: Mar. 2, 2007

(87) PCT Pub. No.: WO2006/073290

PCT Pub. Date: Jul. 13, 2006

(65) Prior Publication Data

US 2007/0191482 A1    Aug. 16, 2007

(30) Foreign Application Priority Data

Jan. 6, 2005    (KR)    .................. 10-2005-0001403

(51) Int. Cl.
*C07C 211/63*    (2006.01)
*A61K 31/14*    (2006.01)
(52) U.S. Cl. .................. 564/282; 564/283; 564/289
(58) Field of Classification Search .................. None
See application file for complete search history.

(56) References Cited

U.S. PATENT DOCUMENTS

| 6,331,571 | B1 | 12/2001 | Jerussi et al. |
| 2004/0068018 | A1 | 4/2004 | Lee et al. |
| 2007/0191481 | A1 | 8/2007 | Lim et al. |
| 2007/0191489 | A1 | 8/2007 | Lim et al. |

FOREIGN PATENT DOCUMENTS

| WO | WO 95/21615 A1 | 8/1995 |
| WO | WO 98/13034 A1 | 4/1998 |
| WO | WO 00/56310 A1 | 9/2000 |
| WO | WO 00/56313 A1 | 9/2000 |

OTHER PUBLICATIONS

Database Caplus on STN, Acc. No. 2004:965047, Lulla et al., WO 2004096202 (Nov. 11, 2004) (abstract).*

(Continued)

*Primary Examiner*—Brian J Davis
(74) *Attorney, Agent, or Firm*—Sterne, Kessler, Goldstein & Fox P.L.L.C.

(57) ABSTRACT

Disclosed is a novel dicarboxylic acid salt of sibutramine, which has good physicochemical properties. Also disclosed are a method of preparing the compound and a pharmaceutical composition comprising the compound.

8 Claims, 4 Drawing Sheets

OTHER PUBLICATIONS

Database Caplus on STN, Acc. No. 2001:526047, Senanayake et al., WO 2001051453 (Jul. 19, 2001) (abstract).*

Database Caplus on STN, Acc. No. 2001:565912, Fu et al., CN 1274714 (Nov. 29, 2000) (abstract).*

International Search Report for International Application No. PCT/KR2006/000071, mailed Apr. 14, 2006, Korean Intellectual Property Office, Republic of Korea.

Office Action for U.S. Appl. No. 10/580,136, Lim et al., 35 U.S.C. § 371 date: Mar. 2, 2007, International Filing Date: Jan. 6, 2006, mailed on Oct. 4, 2007.

Database Caplus, Accession No. 2004:690754, Document No. 141:179571, record for Athayde, A., "Preparation of sibutramine hydrogensulfate," Brazilian Patent Application No. 2001005486, (2004).

Database Delphion, record for Athayde, A., "Process is for obtaining sulphate of 1-(4-chlorophenyl)-N,N-dimethyl-alpha-(2-methylpropyl)-cyclobutanomethamine and its isomers," Brazilian Patent Application No. 2001000005486, (2003).

Database Caplus, Accession No. 1987:623314, Document No. 107:223314, record for Jeffrey et al., "N,N-dimethyl-1-[1-(4-chlorophenyl)cyclobutyl]-3-methylbutylamine hydrochloride monohydrate for use in treating depression," Great Britain Patent No. 2184122, (1987).

Office Action for U.S. Appl. No. 10/580,135, Lim et al., 35 U.S.C. § 371 date: Mar. 2, 2007, International Filing Date: Jan. 6, 2006, mailed on Oct. 4, 2007.

* cited by examiner

DICARBOXYLIC ACID SALT OF SIBUTRAMINE

TECHNICAL FIELD

The present invention relates to a novel dicarboxylic acid salt of sibutramine, a method of preparing the compound, and a pharmaceutical composition comprising the compound as an effective ingredient.

BACKGROUND ART

Sibutramine (N-[1-[1-(4-chlorophenyl)cyclobutyl]-3-methylbutyl]-N,N-dimethylamine), which is a inhibitor of 5-hydroxytryptamine and noradrenaline reuptake in vivo (Neuropharmacology, 28, p 129-134), is useful in the treatment of depression, Parkinson's disease, obesity, insulin-independent diabetes mellitus, epilepsy, and the like. In addition, sibutramine reduces body weight gain by a dual action to reduce food intake by enhancing satiety and to increase energy expenditure by stimulating heat generation (Int. J. Obesity, 19, p 145; Brit. J. Pharmacol. 114, p 388). The therapeutic use of sibutramine in depression is described in British Patent Specification 2098602. The therapeutic use of sibutramine in Parkinson's disease is disclosed in International Pat. Publication No. WO88/06444. The therapeutic use of sibutramine in cerebral function disorders is disclosed in U.S. Pat. No. 4,939,175. The use of sibutramine hydrochloride in the treatment of obesity is disclosed in European Pat. No. 397831. Also, International Pat. Publication No. WO95/20949 discloses the use of sibutramine for improving impaired glucose tolerance or glucose tolerance in patients suffering from insulin-independent diabetes mellitus.

Typically, the preparation of salts having pharmaceutically useful physical properties must satisfy the following physicochemical criteria: (1) good solubility, (2) good stability, (3) good non-hygroscopicity and (4) compressibility into tablet form.

However, Korean Pat. Publication No. 94-8913 states that sibutramine hydrochloride has been known to contain a variable amount of water and thus be hygroscopic, and that non-hygroscopic sibutramine can be obtained by preparing sibutramine hydrochloride in a monohydrate form. Sibutramine hydrochloride monohydrate has been prepared by brining it into contact with a medium consisting of water or a medium containing water. Since sibutramine is difficult to purify due to its low melting point, it is preferable to use a crystalline material capable of being purified by recrystallization in order to prepare a pharmaceutical composition comprising sibutramine. Korean Pat. Publication No. 1990-0000274 discloses that sibutramine is utilized as salts formed with acids providing non-toxic acid addition salts containing pharmaceutically acceptable anions, for example, in the form of hydrochloride, malate, acetate, citrate, fumarate, tartrate, succinate, aspartate or glutmate salt.

However, since sibutramine hydrochloride is difficult to handle pharmaceutically due to its hygroscopic nature, it is undesirable to use sibutramine hydrochloride for preparing medicaments. In the preparation of medicaments, a constant weight of an active compound should be contained in each dosage form, but an active ingredient absorbing water from the surrounding environment makes it difficult to achieve such consistency. Korean Pat. Publication No. 94-8913 discloses that when sibutramine hydrochloride is prepared in a monohydrate form, a non-hygroscopic product is obtained, which is suitable for the preparation of capsules, tablets and other pharmaceutical dosage forms. This patent publication describes that sibutramine hydrochloride monohydrate can be prepared by contacting sibutramine hydrochloride with a medium consisting of or containing water, which is a water-immiscible solvent or a water-miscible solvent.

The currently used sibutramine hydrochloride monohydrate is prepared by a complicated process including adding a predetermined amount of water to a reaction mixture, or including preparing sibutramine hydrochloride anhydrate and suspending the sibutramine hydrochloride anhydrate in a water-containing solvent for a long time with agitation. In addition, since sibutramine hydrochloride monohydrate has relatively low solubility between pH 1.0 and pH 7.4, substitute salts having better solubility need to be developed in order to improve the bioavailability of sibutramine.

In this regard, intensive and through research into the development of novel salts of sibutramine, capable of solving the problems encountered in the prior art, conducted by the present inventors, resulted in the finding that among dicarboxylic acid salts of sibutramine, sibutramine oxalate and sibutramine malonate in anhydrous forms, which do not require a complicated process for preparing a hydrate, possess remarkably high solubility in water, and also exhibit non-hygroscopicity and stability.

DISCLOSURE OF THE INVENTION

It is therefore an object of the present invention to provide a dicarboxylic acid salt of sibutramine.

It is another object of the present invention to provide a method of preparing the dicarboxylic acid salt of sibutramine.

It is a further object of the present invention to provide a pharmaceutical composition for treating and preventing pathological states of obesity and related disorders, comprising the dicarboxylic acid salt of sibutramine as an active ingredient. It is yet another object of the present invention to provide a pharmaceutical composition for treating depression, Parkinson's disease, insulin-independent diabetes mellitus or epilepsy, comprising the dicarboxylic acid salt of sibutramine as an active ingredient.

It is yet another object of the present invention to provide a method of treating and preventing pathological states of obesity and related disorders, and a method of treating depression, Parkinson's disease, insulin-independent diabetes mellitus or epilepsy, these methods being based on administering the pharmaceutical composition comprising the dicarboxylic acid salt of sibutramine as an active ingredient.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 1:
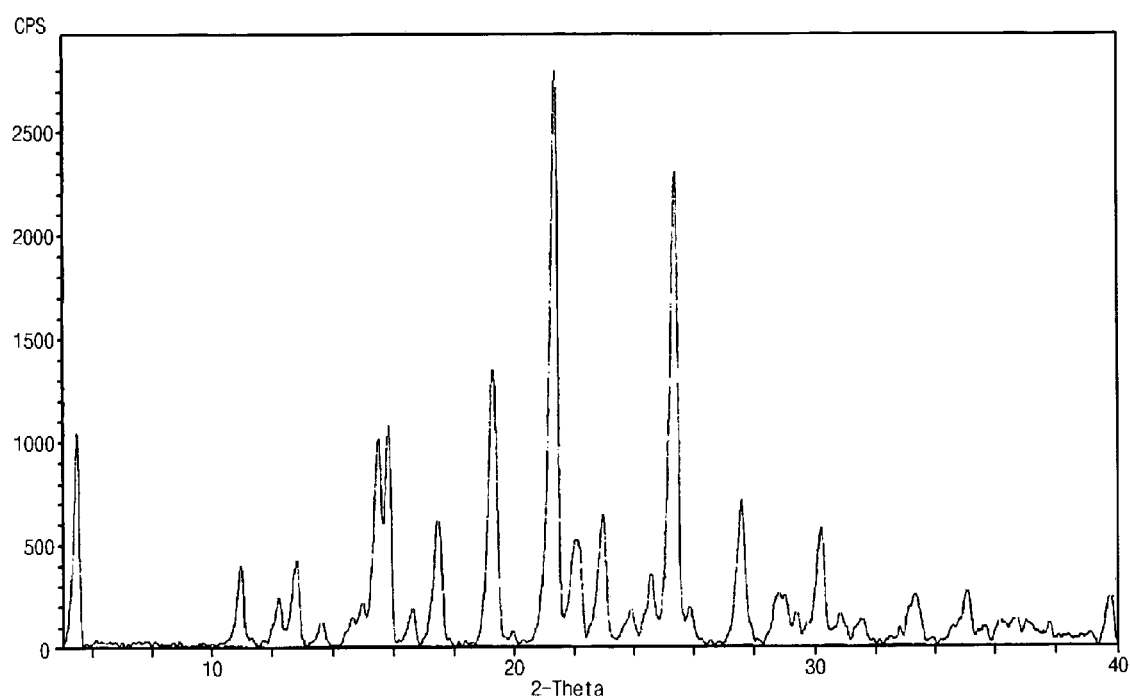
FIG. 1 is a powder X-ray diffraction spectrum of sibutramine oxalate according to the present invention.
Figure 2:
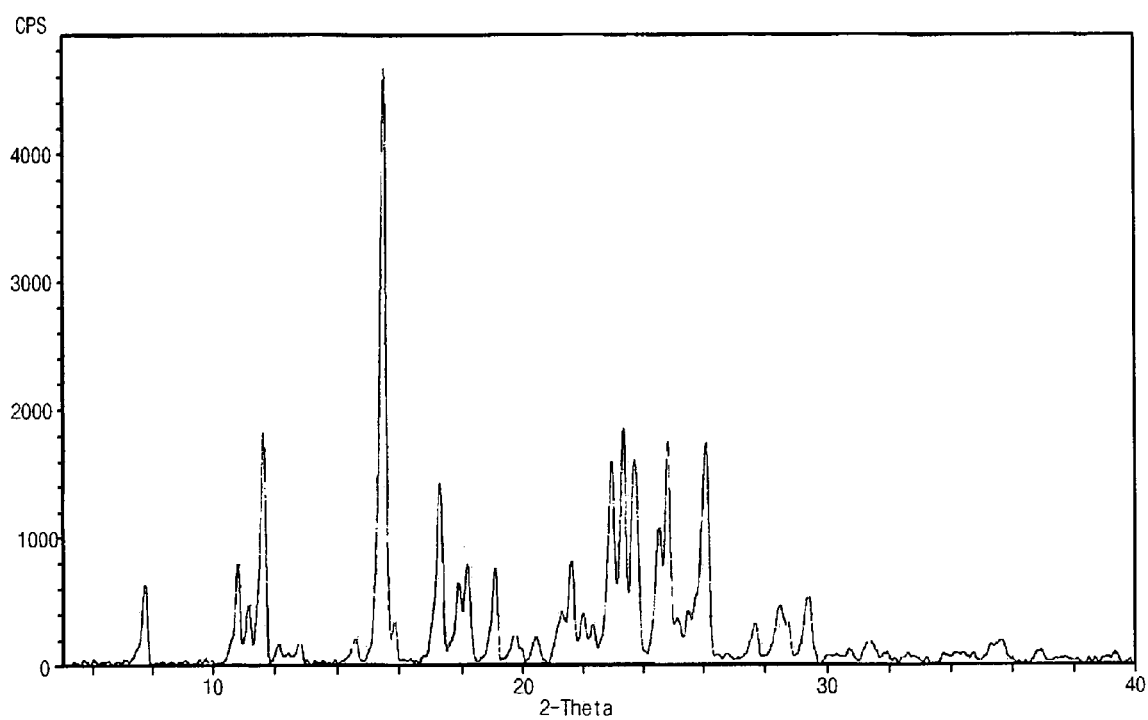
FIG. 2 is a powder X-ray diffraction spectrum of sibutramine malonate according to the present invention.
Figure 3:
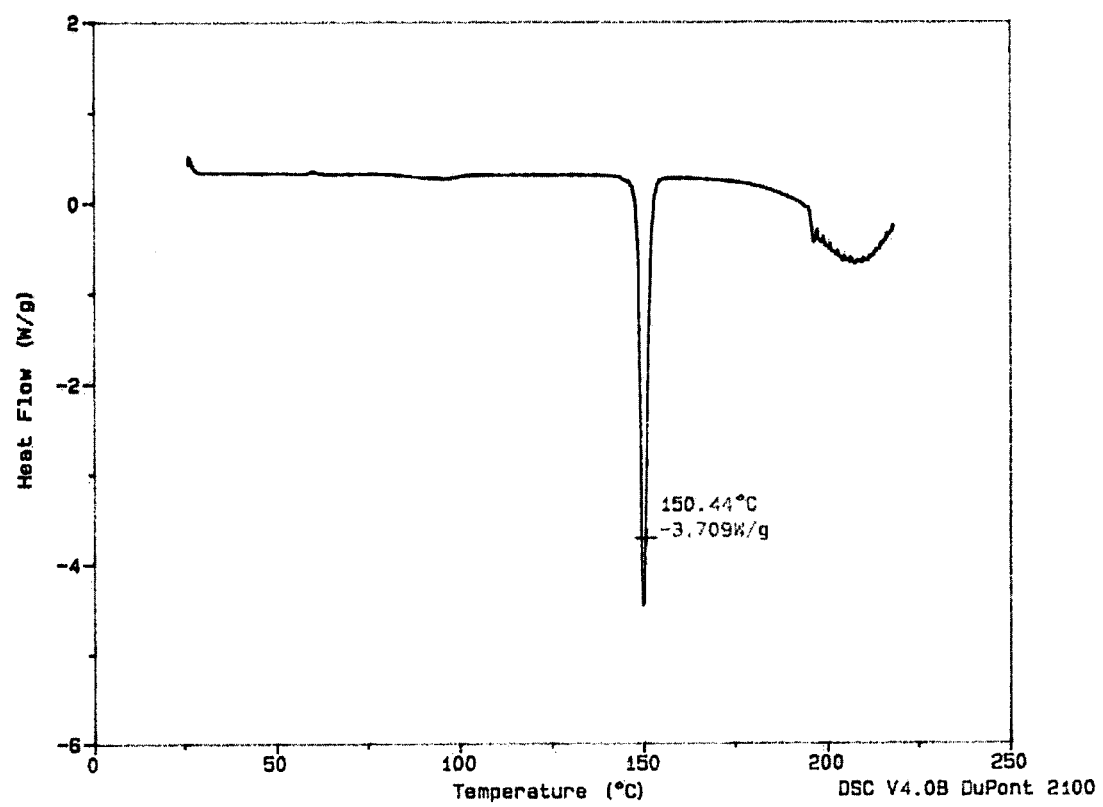
FIG. 3 is a differential scanning calorimeter thermogram of sibutramine oxalate according to the present invention.
Figure 4:
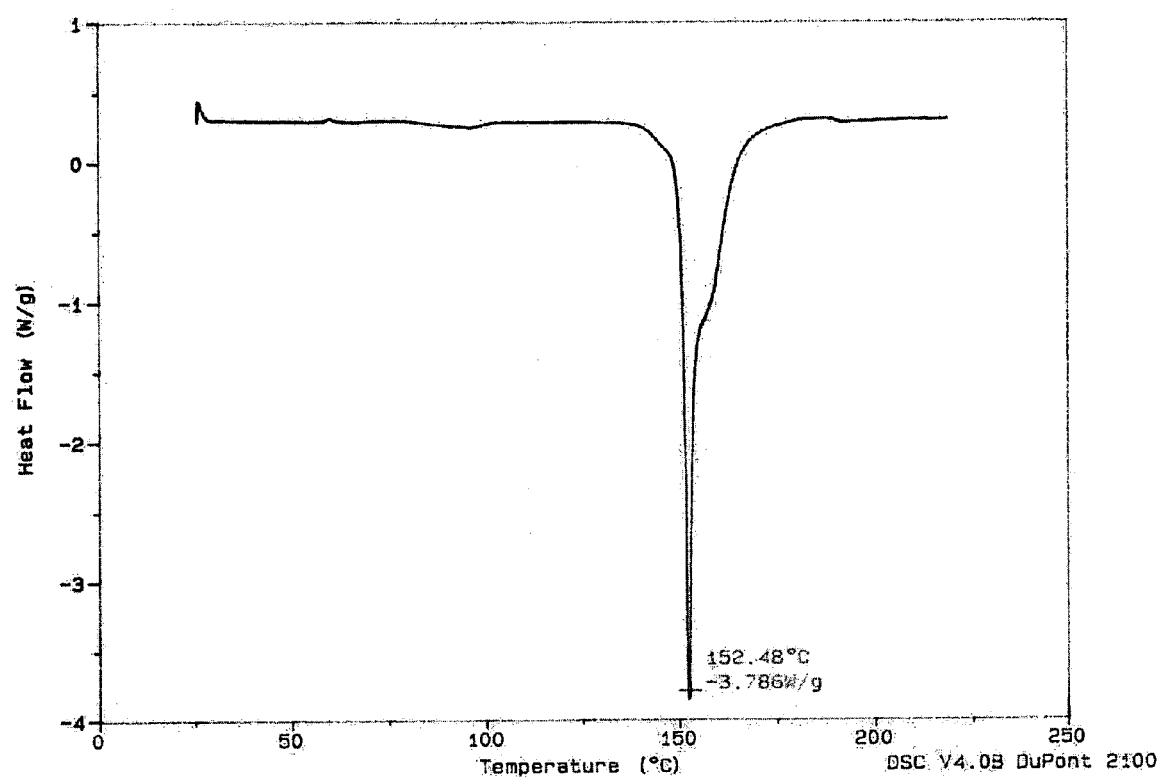
FIG. 4 is a differential scanning calorimeter thermogram of sibutramine malonate according to the present invention.

In one aspect, the present invention relates to a dicarboxylic acid salt of sibutramine, represented by the following Chemical Formula 1:

[Chemical Formula 1]

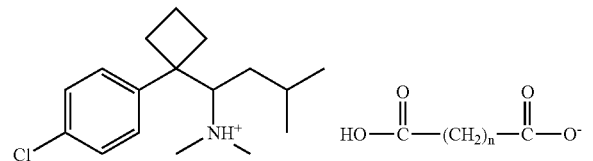

wherein, n is an integral number of 0 or 1.

The compound of Chemical Formula 1 includes sibutramine oxalate represented by Chemical Formula 2, below, and sibutramine malonate represented by Chemical Formula 3, below.

[Chemical Formula 2]

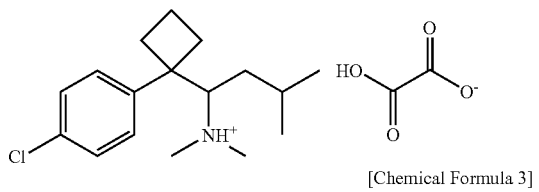

[Chemical Formula 3]

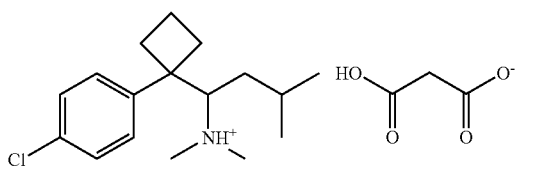

The term "sibutramine", as used herein, refers to racemic sibutramine, unless otherwise noted.

The sibutramine oxalate and sibutramine malonate according to the present invention exhibit remarkably high solubility in water compared to the known sibutramine hydrochloride monohydratand, and also display non-hygroscopicity and chemical stability to heat and light. In particular, oxalic acid and malonic acid used in the preparation of salts are advantageous because they have high safety and low toxicity, relative to hydrochloric acid used in the preparation of sibutramine hydrochloride monohydrate. These acids are pharmaceutically acceptable salts which have been used in various medicaments, and especially, have been safely used in medicines for treating circulatory disorders, including nafronyl, naftidrofuryl and perazine.

TABLE 1

|  | $LD_{50}$ in mouse (i.p.) | $LD_{50}$ in rat (oral) | Remarks |
|---|---|---|---|
| HCl | 40 mg/kg | 900 mg/kg |  |
| Malonic acid | 300 mg/kg | 1310 mg/kg |  |
| Oxalic acid | 155 mg/kg | — | Sodium salt |

The dicarboxylic acid salts of sibutramine according to the present invention may be crystalline or non-crystalline. Crystalline forms of the dicarboxylic acid salts of sibutramine are preferred in consideration of physical properties such as non-hygroscopicity and thermodynamical stability.

In detail, the crystalline sibutramine oxalate of Chemical Formula 2 is characterized by having an X-ray diffraction pattern in which peaks ($I/I_0 \geq 200$) appear at $2\theta$ values of 5.46, 10.92, 12.16, 12.74, 14.92, 15.44, 15.78, 17.4, 19.24, 21.3, 22.0, 22.92, 24.54, 25.3, 25.8, 27.52, 28.74, 28.92, 30.12, 33.26, 35.04, and 39.76.

The crystalline sibutramine malonate of Chemical Formula 3 is characterized by having an X-ray diffraction pattern in which peaks ($I/I_0 \geq 200$) appear at $2\theta$ values of 7.7, 10.74, 11.08, 11.56, 15.42, 15.78, 17.24, 17.84, 18.1, 19.02, 19.68, 21.54, 21.9, 22.24, 22.88, 23.26, 23.64, 24.44, 24.72, 26.0, 27.6, 28.4, 28.62, and 29.3.

In anther aspect, the present invention relates to a method of preparing the dicarboxylic acid salt of sibutramine.

In detail, the present invention includes a method of preparing a dicarboxylic acid salt of sibutramine, comprising reacting sibutramine with a dicarboxylic acid selected from among oxalic acid and malonic acid in an inert solvent.

In a detailed practice, the reaction of sibutramine with oxalic acid or malonic acid takes place according to Reaction 1, below.

[Reaction 1]

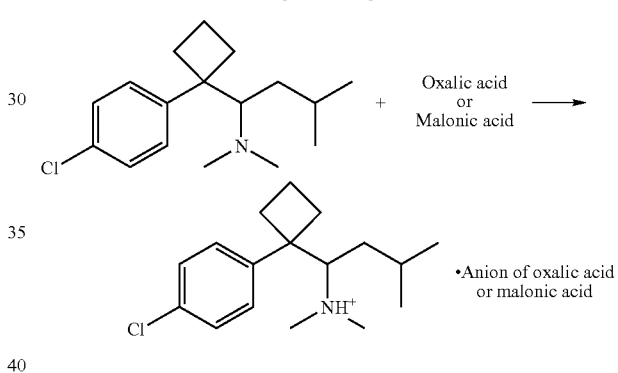

In the method, oxalic acid and malonic acid may be used in an amount of 1 to 2 molar equivalents, and preferably 1.1 to 1.2 molar equivalents, relative to one molar equivalent of sibutramine. Typically, oxalic acid or malonic acid is added in a solid state to an organic solvent in which sibutramine is dissolved, dissolved in an organic solvent in which sibutramine is dissolved, or added in droplets thereto after being dissolved in another organic solvent.

In the method, the organic solvent may be used in an amount of 3 to 20 ml, and preferably 5 to 15 ml, relative to 1 g of sibutramine.

The organic solvent used in the method is a mixture of one or more ester solvents, selected from the group consisting of ethyl acetate, n-propyl acetate, isopropylacetate and n-butyl acetate, and one or more alcohol solvents, selected from the group consisting of methanol, ethanol, propanol, butanol and isopropanol, or is one selected from among the solvents.

The method is performed at a reaction temperature ranging from 0° C. to the boiling point of a solvent, and preferably at a temperature of 15 to 35° C. Also, after oxalic acid or malonic acid is added, the reaction is preferably allowed to take place for 0.5 to 6 hours.

Sibutramine oxalate and sibutramine malonate of Chemical Formulas 2 and 3, respectively, prepared according to the method have greatly enhanced solubility in water while exhibiting almost the same non-hygroscopicity and stability to water and heat as does sibutramine hydrochloride monohydrate, which is conventionally used as an acid addition salt. Owing to such enhanced water solubility, the dicarboxylic acid salt of sibutramine according to the present invention has a good release rate characteristic from a composition comprising the same, and thus has better bioavailability.

The present invention relates to a pharmaceutical composition comprising a therapeutically effective amount of a dicarboxylic acid salt of sibutramine and a pharmaceutically acceptable diluent or carrier, and a method of treating or preventing diseases by administering the composition. In an aspect, the present invention includes a pharmaceutical composition for treating or preventing pathological states of obesity and related disorders, comprising a therapeutically effective amount of a dicarboxylic acid salt of sibutramine and a pharmaceutically acceptable diluent or carrier, and a method of treating or preventing pathological states of obesity and related disorders using this composition.

The present invention also includes a pharmaceutical composition for treating depression, comprising a therapeutically effective amount of a dicarboxylic acid salt of sibutramine and a pharmaceutically acceptable diluent or carrier, and a method of treating depression by administering this composition.

The present invention further includes a pharmaceutical composition for treating or preventing Parkinson's disease, comprising a therapeutically effective amount of a dicarboxylic acid salt of sibutramine and a pharmaceutically acceptable diluent or carrier, and a method of treating or preventing Parkinson's disease by administering this composition.

The present invention still further includes a pharmaceutical composition for treating insulin-independent diabetes mellitus, comprising a therapeutically effective amount of a dicarboxylic acid salt of sibutramine and a pharmaceutically acceptable diluent or carrier, and a method of treating insulin-independent diabetes mellitus by administering this composition.

The present invention still further includes a pharmaceutical composition for treating epilepsy, comprising a therapeutically effective amount of a dicarboxylic acid salt of sibutramine and a pharmaceutically acceptable diluent or carrier, and a method of treating epilepsy by administering this composition.

The pharmaceutical composition comprising the dicarboxylic acid salt of sibutramine according to the present invention as an active ingredient may be preferably administered orally, for example in the form of tablets or capsules.

Tablets may be prepared by mixing an active ingredient with a carrier, a diluent or an excipient and compressing the mixture into tablets. Examples of suitable carriers, diluents or excipients include disintegrators such as starch, sugars and mannitol; fillers and extenders such as calcium phosphate and silicic derivatives; binding agents such as carboxymethyl cellulose and other cellulose derivatives, gelatin and polyvinyl pyrrolidone; and lubricants such as talc, calcium and magnesium stearate, and solid polyethylene glycol. Also, hard or soft gelatin capsules containing an active ingredient, either with or without an additive such as the carriers, diluents or excipients may be prepared according to an ordinary method.

The pharmaceutical composition preferably contains a crystalline dicarboxylic acid salt of sibutramine, represented by Chemical Formula 1, as an active ingredient in an amount of 1 to 50 parts by weight based on 250 parts by weight of the composition. For example, the pharmaceutical composition having a total weight of 250 mg according to the present invention may be prepared in such a manner as to contain 10 mg (based on sibutramine content) of the crystalline dicarboxylic acid salt of sibutramine, represented by Chemical Formula 1, 115 mg of microcrystalline cellulose, 115 mg of lactose, 5 mg of silicon dioxide, and 5 mg of magnesium stearate. However, this composition of the pharmaceutical composition is illustrative, and thus, the scope of the present invention is not limited thereto.

A better understanding of the present invention may be obtained through the following examples which are set forth to illustrate, but are not to be construed as the limit of the present invention.

EXAMPLES

Sibutramine oxalate and sibutramine malonate according to the present invention were prepared, and were compared with sibutramine hydrochloride hydrate for physical properties including hygroscopicity, solubility, stability, light stability and crystallizability. In addition, sibutramine oxalate and sibutramine malonate were formulated into capsules in order to examine their formulability and release patterns.

Reference Example 1

Preparation of Sibutramine Hydrochloride Monohydrate

Sibutramine hydrochloride anhydrate was prepared according to a method described in Korean Pat. Publication No. 90-00274. Then, according to a method described in Korean Pat. Publication No. 94-08913, 10 g of the prepared sibutramine hydrochloride anhydrate was dissolved in a boiling mixture of 110 ml acetone and 1.2 ml water, and the resulting solution was hot-filtered and distilled to remove 80 ml of the solvent, thus reducing the volume of the filtrate. The concentrate was filtered to recover a generated solid. The solid was vacuum-dried, thus obtaining 9.2 g (yield: 87%) of the compound of Chemical Formula 2, which had a melting point of 195° C.

Example 1

Preparation of Sibutramine Oxalate 15 g of sibutramine was dissolved in 60 ml of methanol. Oxalic acid (5.07 g) dissolved in 20 ml methanol was slowly added in droplets to the sibutramine solution at room temperature and agitated for 2 hrs. The resulting solution was cooled to 0° C., agitated for about 2 hrs, and filtered to collect deposited crystals. The crystals were washed with 50 ml of isopropyl ether and vacuum-dried at 50° C., thus obtaining 18 g (yield: 89.7%) of a white target compound.

TABLE 2

| Elemental analysis ($C_{19}H_{28}ClNO_4$) | Unit (%) |
|---|---|
| Measured value | C: 61.88, H: 7.87, N: 3.81, O: 17.63 |
| Theoretical value | C: 61.7, H: 7.63, N: 3.79, O: 17.30 |

Melting point: 150.4° C.

$^1$H-NMR (DMSO-d6): 1.0 (6H, dd), 1.4 (2H, t), 1.6~1.8 (2H, m), 1.9 (1H, m), 2.4 (2H, m), 2.5 (6H, s), 2.6 (2H, m), 2.7 (2H, m), 3.6 (1H, t), 7.5 (4H, dd)

Example 2

Preparation of Sibutramine Malonate 15 g of sibutramine was dissolved in 60 ml of ethyl acetate. Malonic acid (5.72 g) dissolved in 20 ml ethyl acetate was slowly added in droplets to the sibutramine solution at room temperature and agitated for 2 hrs. The resulting solution was cooled to 0° C., agitated for about 2 hrs, and filtered to collect a deposited crystal. The crystal was washed with 50 ml of isopropyl ether and vacuum-dried at 50° C., thus obtaining 19 g (yield: 92.6%) of a white target compound.

TABLE 3

| Elemental analysis ($C_{20}H_{30}ClNO_4$) | Unit (%) |
|---|---|
| Measured value | C: 62.75, H: 8.13, N: 3.67, O: 17.12 |
| Theoretical value | C: 62.57, H: 7.88, N: 3.65, O: 16.67 |

Melting point: 152.4° C.

$^1$H-NMR (DMSO-d6): 0.9 (6H, dd), 1.2 (2H, m), 1.5~1.8 (2H, m), 1.9 (1H, m), 2.2 (2H, m), 2.3 (6H, s), 2.4 (2H, m), 2.5 (2H, m), 3.1 (2H, s), 3.2 (1H, t), 7.4 (4H, m)

Example 3

Non-hygroscopicity Evaluation

The crystalline sibutramine oxalate and sibutramine malonate, prepared in Examples 1 and 2, respectively, and the known sibutramine hydrochloride monohydrate were exposed to humid air at 75% or 95% relative humidity at 25° C. for a period of three days or one week. Then, the water content of the samples was measured using a Karl-Fisher titrator. The results are given in Table 4, below. In Table 4, the water content of an active ingredient is expressed as a percentage of water content by weight (weight %).

TABLE 4

| | | Storage humidity (relative humidity) at 25° C. | |
|---|---|---|---|
| Storage period | Initial | 75% 3 days | 95% 1 week |
| Sibutramine oxalate | 0.02% | 0.03% | 0.02% |
| Sibutramine malonate | 0.03% | 0.02% | 0.03% |
| Sibutramine HCl monohydrate | 5.49% | 5.49% | 5.5% |

As shown in Table 4, sibutramine oxalate and sibutramine malonate did not absorb moisture even in a humid atmosphere of 95% relative humidity, indicating that these compounds have non-moisture-absorbing properties.

Example 4

Solubility Evaluation

The crystalline sibutramine oxalate and sibutramine malonate, prepared in Examples 1 and 2, respectively, and the known sibutramine hydrochloride monohydrate were evaluated for solubility in distilled water and at several pH values. The results are given in Table 5, below.

TABLE 5

| | Salt forms of sibutramine | | | |
|---|---|---|---|---|
| Solvent | HCl monohydrate (mg/ml) | Oxalate (mg/ml) | Malonate (mg/ml) | Remarks |
| Distilled water | 26.18 | 35.76 | 44.51 | Dissolved at 37° C. |
| pH 1.2 | 13.36 | 40.64 | 85.72 | |
| pH 4.0 | 9.58 | 25.46 | 32.87 | |
| pH 5.3 | 6.58 | 54.79 | 17.57 | |
| pH 6.8 | 23.14 | 34.04 | 55.42 | |
| pH 7.4 | 9.2 | 23.41 | 34.63 | |

As shown in Table 5, sibutramine oxalate and sibutramine malonate had high solubility in distilled water and at several pH values. In particular, these compounds had high solubility at pH 7.4 within the range of blood pH, indicating that they have good bioavailability.

Example 5

Evaluation of Stability to Heat and Light

The stability of an active ingredient used in a pharmaceutical composition to heat and light is a very important physical property during formulation into tablets and capsules and long-term storage. In this regard, sibutramine oxalate and sibutramine malonate were evaluated for stability at a high temperature and in the presence of light for a predetermined period of time, and were compared with sibutramine hydrochloride monohydrate for heat stability and photostability. In detail, each compound was stored at 60° C. After 1, 2 and 4 weeks, the residual proportion of the initial level of an active ingredient was measured by high performance liquid chromatography (HPLC). The results are given in Table 6, below. Also, fluorescent light was radiated at 25° C. using a light stability test chamber suitable for the ICH guideline, and after 1, 2 and 4 weeks, the residual proportion of the initial level of an active ingredient was measured by HPLC. The results are given in Table 7, below.

TABLE 6

| | Storage period | | | |
|---|---|---|---|---|
| | Initial | 1 week | 2 weeks | 4 weeks |
| HCl monohydrate | 1.000 | 1.000 | 0.999 | 0.999 |
| Oxalate | 1.000 | 1.000 | 0.999 | 0.999 |
| Malonate | 1.000 | 1.000 | 0.999 | 0.999 |

TABLE 7

| | Storage period | | | |
|---|---|---|---|---|
| | Initial | 1 week | 2 weeks | 4 weeks |
| HCl monohydrate | 1.000 | 1.000 | 0.999 | 0.998 |
| Oxalate | 1.000 | 1.000 | 0.999 | 0.999 |
| Malonate | 1.000 | 1.000 | 0.999 | 0.999 |

As shown in Tables 6 and 7, sibutramine oxalate and sibutramine malonate exhibited heat stability and photostability equal to those of sibutramine hydrochloride monohydrate.

Example 6

Preparation of Capsules Containing Sibutramine Oxalate

Ingredients were mixed according to the composition described in Table 8, below, to prepare capsules containing sibutramine oxalate.

TABLE 8

| Ingredients | Content (per capsule) |
| --- | --- |
| Sibutramine oxalate | Amount corresponding to 10 mg of sibutramine |
| Lactose | 115 mg |
| Microcrystalline cellulose | 115 mg |
| Silicon dioxide | 5 mg |
| Magnesium stearate | 5 mg |

The ingredients were mixed and filled into hard capsules using a capsule filling machine (Bosche).

Example 7

Preparation of Capsules Containing Sibutramine Malonate

Ingredients were mixed according to the composition described in Table 9, below, to prepare capsules containing sibutramine malonate.

TABLE 9

| Ingredients | Content (per capsule) |
| --- | --- |
| Sibutramine malonate | Amount corresponding to 10 mg of sibutramine |
| Lactose | 115 mg |
| Microcrystalline cellulose | 115 mg |
| Silicon dioxide | 5 mg |
| Magnesium stearate | 5 mg |

The ingredients were mixed and filled into hard capsules using a capsule filling machine (Bosche).

INDUSTRIAL APPLICABILITY

The dicarboxylic acid salts of sibutramine according to the present invention have good physicochemical properties including non-hygroscopicity, solubility, stability, formulability and crystallizability. Compared to the known sibutramine hydrochloride monohydrate, the dicarboxylic acid salts of sibutramine have advantages of good solubility and simple preparation by a process not requiring an additional procedure for preparing a hydrate. The advantages further include that because the present compounds, present in anhydrous forms, do not change in content due to their non-hygroscopic nature, they guarantee consistency suitable for the preparation of pharmaceutical dosage forms. Thus, the present compounds may be suitable for long-term storage. The present compounds also have enhanced bioavailability.

Moreover, since oxalic acid and malonic acid used in the preparation of the novel dicarboxylic acid salts of sibutramine are less-toxic acids that have been proven to be pharmaceutically safe for long-term use, the novel dicarboxylic acid salts of sibutramine may be suitable for long-term administration with no risk of toxicity.

The invention claimed is:

1. A dicarboxylic acid salt of sibutramine, represented by the following Chemical Formula 1:

Chemical Formula 1

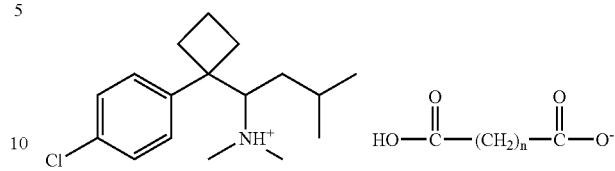

wherein, n is an integral number of 0 or 1.

2. The dicarboxylic acid salt of sibutramine as set forth in claim 1, which is sibutramine oxalate having an X-ray diffraction pattern in which peaks appear at 2θ values of 5.46, 10.92, 12.16, 12.74, 14.92, 15.44, 15.78, 17.4, 19.24, 21.3, 22.0, 22.92, 24.54, 25.3, 25.8, 27.52, 28.74, 28.92, 30.12, 33.26, 35.04, and 39.76.

3. The dicarboxylic acid salt of sibutramine as set forth in claim 1, which is sibutramine malonate having an X-ray diffraction pattern in which peaks appear at 2θ values of 7.7, 10.74, 11.08, 11.56, 15.42, 15.78, 17.24, 17.84, 18.1, 19.02, 19.68, 21.54, 21.9, 22.24, 22.88, 23.26, 23.64, 24.44, 24.72, 26.0, 27.6, 28.4, 28.62, and 29.3.

4. A method of preparing a dicarboxylic acid salt of sibutramine represented by the following Chemical Formula 1:

Chemical Formula 1

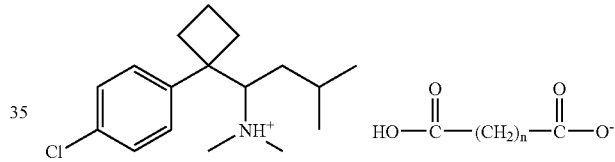

wherein, n is an integral number of 0 or 1 comprising reacting sibutramine with a dicarboxylic acid selected from among oxalic acid and malonic acid in an inert solvent.

5. A pharmaceutical composition comprising a dicarboxylic acid salt of sibutramine represented by the following Chemical Formula 1:

Chemical Formula 1

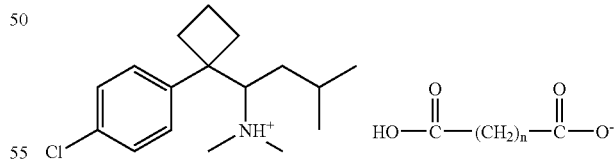

wherein, n is an integral number of 0 or 1 as an effective ingredient and a pharmaceutically acceptable diluent or carrier.

6. The pharmaceutical composition as set forth in claim 5, which is formulated into tablets or capsules.

7. A method of treating obesity, depression, Parkinson's disease, insulin-independent diabetes mellitus or epilepsy, comprising administering the pharmaceutical composition comprising the dicarboxylic acid salt of sibutramine represented by the following Chemical Formula 1:

Chemical Formula 1
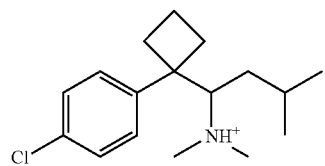 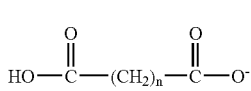
wherein, n is an integral number of 0 or 1 as an effective ingredient.
8. The pharmaceutical composition as set forth in claim 5, wherein the composition is for treating obesity, depression, Parkinson's disease, insulin-independent diabetes mellitus, or epilepsy.
\* \* \* \* \*